(12) United States Patent
Sacherer et al.

(10) Patent No.: US 8,187,537 B2
(45) Date of Patent: May 29, 2012

(54) DIAGNOSTIC TEST UNIT WITH A CONTAINER FOR TEST CARRIERS

(75) Inventors: Klaus-Dieter Sacherer, Kirchheim (DE); Wolfgang Ditscher, Kaiserslautern (DE); Ralf Steinbrück, Mannheim (DE); Werner Ruhl, Limburgerhof (DE); Klaus Schöttle, Willstätt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 684 days.

(21) Appl. No.: 12/257,752

(22) Filed: Oct. 24, 2008

(65) Prior Publication Data

US 2009/0098644 A1 Apr. 16, 2009

Related U.S. Application Data

(63) Continuation of application No. PCT/EP2007/054267, filed on May 2, 2007.

(30) Foreign Application Priority Data

May 6, 2006 (EP) .................... 06009396

(51) Int. Cl.
  *G01N 21/00* (2006.01)
  *B65H 75/30* (2006.01)
(52) U.S. Cl. .................. 422/66; 422/554; 242/381.2
(58) Field of Classification Search .................. 422/554, 422/66; 242/381.2
See application file for complete search history.

(56) References Cited

U.S. PATENT DOCUMENTS

| | | | |
|---|---|---|---|
| 4,218,421 A | 8/1980 | Mack et al. | |
| 7,378,270 B2 * | 5/2008 | Azarnia et al. | 435/287.2 |
| 2002/0076349 A1 * | 6/2002 | Aitken et al. | 422/58 |
| 2007/0065340 A1 * | 3/2007 | Sacherer | 422/58 |

FOREIGN PATENT DOCUMENTS

| | | |
|---|---|---|
| EP | 1 321 769 A1 | 6/2003 |
| WO | 01/23885 A1 | 4/2001 |
| WO | 2004/056269 A1 | 7/2004 |
| WO | 2006/002432 A1 | 1/2006 |
| WO | 2006/059241 A2 | 6/2006 |

OTHER PUBLICATIONS

Translation of International Patent Application PCT/EP2007/054267 International Preliminary Report on Patentability mailed Aug. 27, 2008.
International Patent Application PCT/EP2007/054267 International Preliminary Report on Patentability mailed Aug. 27, 2008.
International Patent Application PCT/EP2007/054267 International Search Report mailed Jul. 31, 2007.

* cited by examiner

*Primary Examiner* — Lore Jarrett
(74) *Attorney, Agent, or Firm* — Woodard, Emhardt, Moriarty, McNett & Henry LLP

(57) ABSTRACT

The invention concerns a diagnostic test unit for analysing a body fluid comprising a test carrier (test tape 10; test strips 12) provided with test fields (38) for applying the body fluid and a container (14) containing the test carrier, wherein an opening (18) of the container (14) is at least in some areas bordered by a seal (16). According to the invention it is proposed that the opening (18) is screened by a closing foil (22) from the surroundings of the container (14) and that the test tape (10) or a test strip (12) to be dispensed is passed through a passage gap (20) between the closing foil (22) and the seal (16).

27 Claims, 3 Drawing Sheets

DIAGNOSTIC TEST UNIT WITH A CONTAINER FOR TEST CARRIERS

CROSS REFERENCE TO RELATED APPLICATIONS

This application is a continuation of International Application No. PCT/EP2007/054267, filed May 2, 2007, which claims the benefit of European Patent Application No. EP 06009396.0, filed May 6, 2006, both of which are hereby incorporated by reference in their entirety.

BACKGROUND

The invention concerns a diagnostic test unit for analysing a body fluid in particular for blood sugar tests according to the preamble of claims 1 and 7.

Such test units can be used especially as consumables to determine blood sugar in automated hand-held devices which can be used even by laymen to carry out the necessary analytical steps in a simple and rapid manner. A plurality of test fields provided with a suitable test chemistry are arranged successively on the wound analytical tape. Alternatively individual test strips can also be removed from a magazine. The body fluid is applied to a test field provided in this manner in order to then enable a detection to be carried out locally by an optical analysis.

Various sealing concepts are described in WO 2004/056269 A1 of the applicant in order to protect the unused part of a test tape in a container against damaging environmental influences and at the same time allow the tape to be transported for the successive provision of the test fields. In this connection the test tape is dispensed over an aperture between the seal and a housing wall where the sealing elements are located on the profiled side of the test field whereas the rear wall is rigid. A separate filling means is provided for the assembly and filling.

EP-A-1321769 describes a dispensing apparatus for the use of test strips in which a single strip is provided by a translational movement through and between a seal and a rigid housing cover from a stored stack. A slide drawer is provided to fill it with a stack of strips which has to be separately sealed.

A disposable cassette unit is known from WO 2006/002432 A1 which comprises a housing, strip-shaped test sensors located therein, a dispensing mechanism and a movable seal. The so-called "duckbill seal" forms a projecting circumferential sealing lip which under slight deformation rests on both sides against the dispensed test strip. A problem in this connection is the inadequate contact pressing force which decreases even further as the period of use increases due to material fatigue. An adequate sealing function is not ensured especially in the case of different height profiles of the test material. A similar sealing design using sealing lips which loosely rest against one another is also known from WO 2006/059241 A2 for a tape containing electrochemical sensors.

SUMMARY

On this basis the object of the invention was to avoid the disadvantages occurring in the prior art and improve a generic test unit for disposable use in hand-held devices such that a high stability in storage and in use is achieved while being simple to manufacture.

The combination of features stated in claims 1 and 7 is proposed to achieve this object. Advantageous embodiments and further developments of the invention are derived from the dependent claims.

The invention is based on the idea of also using a sealing foil as a sealing element. Accordingly it is proposed according to the invention that the opening is screened by a closing foil against the surroundings of the container and that the test tape or the test strip to be dispensed is guided through a passage gap between the closing foil and the seal. This creates a passage seal using simple means and the formation of a passage gap between the flexible foil and a preferably elastomeric seal offers particular advantages for production and when in use. A reliable screening against moisture can be achieved by sealing the foil which, due to its flexibility, also allows height-profiled test materials to pass through substantially unhindered. A particular advantage is due to the fact that the sealable opening allows the filling as well as the dispensing of test and auxiliary materials without having to implement additional sealing measures. Thus the filling and dispensing opening are on one plane which is tightly screened by the closing foil.

The test tape is advantageously inserted into the container through the opening preferably in the form of a tape roll which makes the loading and sealing particularly simple.

Another improvement with regard to the sealing effect can be achieved by means of the fact that the test tape has free carrier sections between successive test fields and that a test field-free carrier section is in the passage gap in the stored state.

In a particularly preferred embodiment the container is formed by a tape cassette wherein the test tape can be transported out of a storage chamber over an application site into a waste and the opening is located in the area of the storage chamber.

Another improvement in handling results from the fact that the smooth rear side of the test tape facing away from the test fields glides over the seal whereas the front side of the test tape carrying the raised test fields runs towards the edge of the flexible closing foil.

When a plurality of disposable test strips are used, there are particular assembly advantages when the test strips are introduced into the container through the opening preferably as a stack of strips.

Another improvement can be achieved by means of the fact that the container is formed by a strip magazine where the test strips can be individually pushed out of a storage chamber. In this case it is advantageous when the rear side of a particular test strip which faces away from the test field glides over the seal and the front side runs against the flexible closing foil when it is dispensed.

In general before the closing foil is applied, the opening can form an inlet for particular insert parts of the container and especially for desiccants that are introduced through the opening into the container preferably in the form of functional composite injection-moulded parts. As already mentioned a tape roll or stack of strips can also be inserted without difficulty into the container as prefabricated insert parts before the opening is sealed.

In order to effectively avoid even small leakages it is advantageous when the closing foil is held by a pressing element under surface pressure to minimize the passage gap towards the seal. The pressing element advantageously comprises a spring and in particular a leaf spring which preferably consists of high-grade steel.

Another simplification arises from the fact that when the closing foil is applied, the passage gap is kept free by a section of the test tape or of a test strip or by an appropriately dimensioned insert whereas in the remaining area the closing foil is joined along a sealing line with the container and/or the seal in a material-tight manner. The closing foil is also preferably sealed onto the test tape or insert present in the gap such that the opening remains circumferentially sealed in a material-tight manner until first use. This can be achieved in a particularly simple manner by means of the fact that the closing foil is formed by a carrier material preferably made of aluminium which is provided with a heat-seal coating. Furthermore, it is advantageous when the closing foil is sealed onto or integrally applied to a preferably flat ring face on the container which borders the opening where at least one segment of the ring face is formed by the seal and the closing foil completely spans the entire surface of the ring face.

For the manufacturing technology it is advantageous when the seal is formed preferably from a thermoplastic elastomer (TPE) as a single component injection-moulded part or as a two-component injection-moulded part in combination with the container.

In order to additionally improve the storage stability, it is advantageous when the container loaded with the test tape or the test strips is stored in a material-tight outer packaging which is to be opened for use.

The invention also concerns a hand-held device for analysing a body fluid and in particular for blood sugar tests with a receiving compartment for inserting a test unit as described above.

BRIEF DESCRIPTION OF THE DRAWINGS

The invention is further elucidated in the following on the basis of the embodiment examples shown schematically in the drawing.

DESCRIPTION OF THE SELECTED EMBODIMENTS

Figure 1:
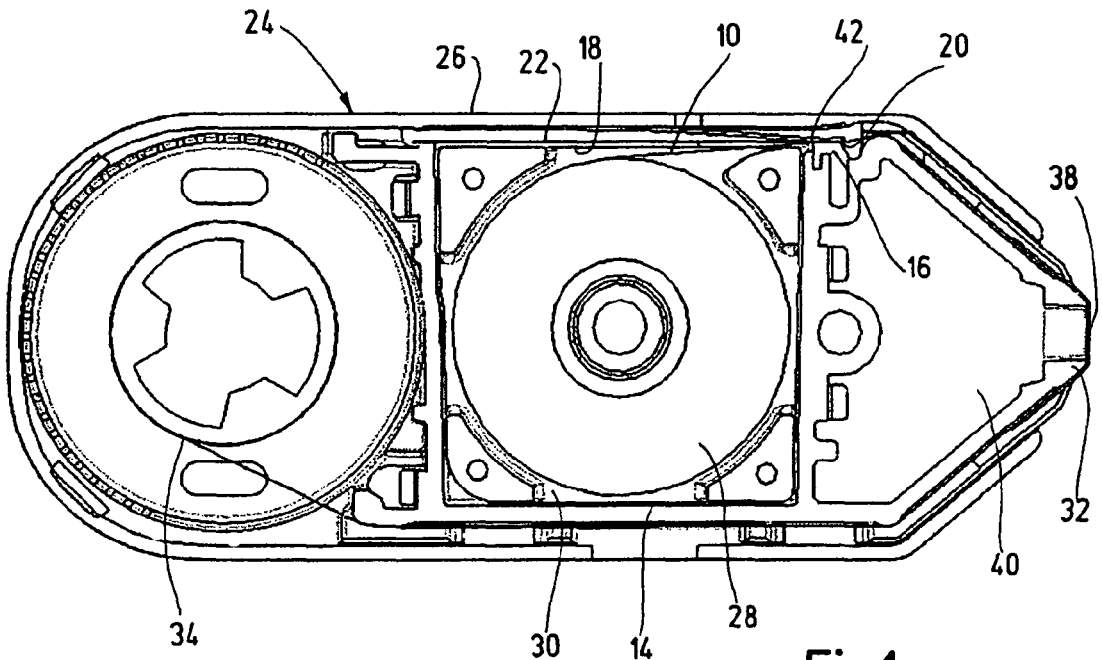
FIG. 1 shows a test tape cassette for blood sugar tests with a foil seal in an opened side-view.

The diagnostic test units shown in the drawing allow a large number of blood sugar determinations to be carried out locally on blood samples taken by the patients themselves. In order to screen the test carriers stored as a test tape 10 or test strips 12 from environmental influences, a container 14 is provided which has an opening 18 the edge of which is bordered by a seal 16 and is sealed by a closing foil 22 while keeping a passage gap 20 free to pass through the test carrier.

FIG. 1 shows a tape cassette 24 consisting of a cassette body 26 and a test tape 10 accommodated therein. The test tape 10 is stored in a storage chamber 30 delimited by the container 14 in the form of a supply roll 28 and can be wound onto a waste spool 34 while being deflected over an application tip 32 which is accessible from outside.

Figure 2:
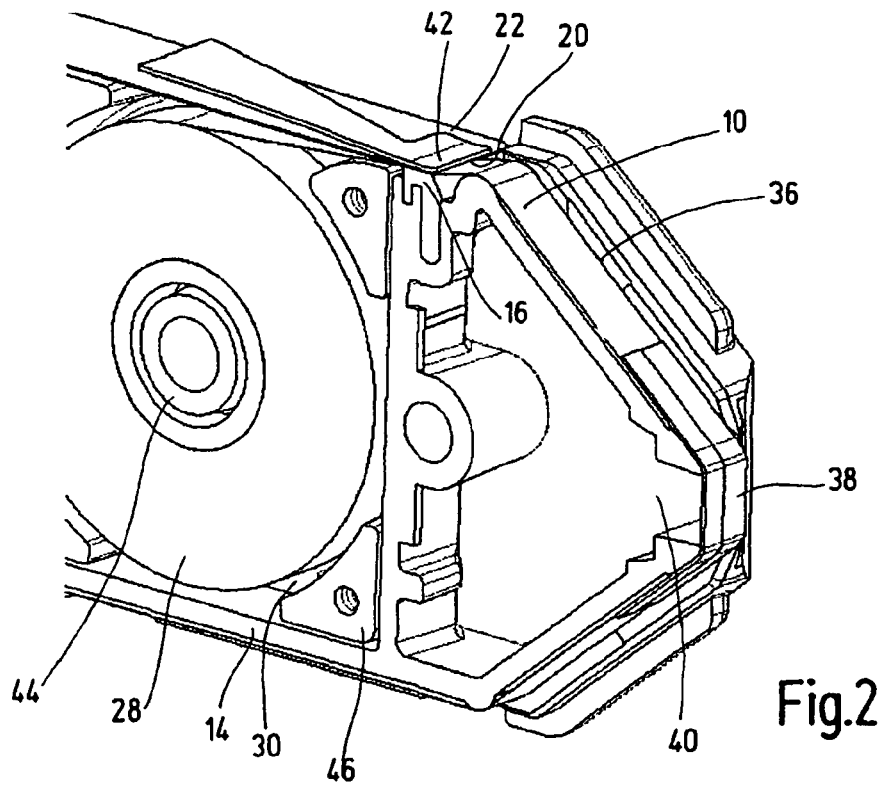
FIG. 2 shows a section of the test tape cassette according to FIG. 1 in a perspective view.

As also shown in FIG. 2, the test tape 10 has a thin carrier foil or tape 36 along which a plurality of test fields 38 are configured spaced apart from one another. Thus the test fields 38 can be positioned as required in the area of the application tip 32 by advancing the tape and body fluid (blood or optionally also tissue fluid) can be selectively applied there.

The test fields 38 are glued onto the carrier tape 36 as prefabricated label-like cut-out parts and are consequently raised above the tape. They can contain dry reagents which react with the analyte (glucose) while changing their colour and thus allow an optical detection. For this purpose a measuring unit in the device (not shown) can engage in the head region 40 of the cassette 24.

In order to protect the moisture-sensitive test chemistry over a longer storage period, the opening 18 of the storage chamber 30 is sealed in a material-tight manner by the closing foil 22 except for the passage gap 20 located over the seal 16. In the storage state a test field-free carrier section of the carrier tape 36 is located in the gap area to which the closing foil 22 can be detachably connected before first use in order to minimize leakages. A pressing element 42 which exerts a surface pressure on the closing foil 22 in the direction of the seal 16, is provided in order to further improve the sealing action. In this manner the carrier tape 36 which lies in between is pressed into the soft seal 16 which encloses and seals the rear side of the tape.

When the tape is advanced the smooth rear side of the carrier tape 36 glides over the seal 16 while an elevated test field 38 that passes through runs against the edge of the flexible closing foil 22 and lifts the foil against the restoring force of the pressing element 42. The shore hardness of the seal 16 and its constructive design, the coefficients of friction of the materials used and the surface pressure of the pressing element 42 should be exactly matched to achieve a seal at a defined withdrawal force.

The storage chamber 30 sealed in this manner can be conditioned by inserting desiccants in order to further optimize its use. In this connection desiccant composite injection-moulded parts can fulfil an additional function for example as an assisting element when inserting and positioning the supply roll 28. In particular bearing pins 44 or supporting parts 46 can be moulded. A high moisture holding capacity and uptake rate can also be achieved with such compound materials. The storage stability before use can be further increased by a suitable outer packaging of the entire cassette 24 by a tight foil material.

Figure 3:
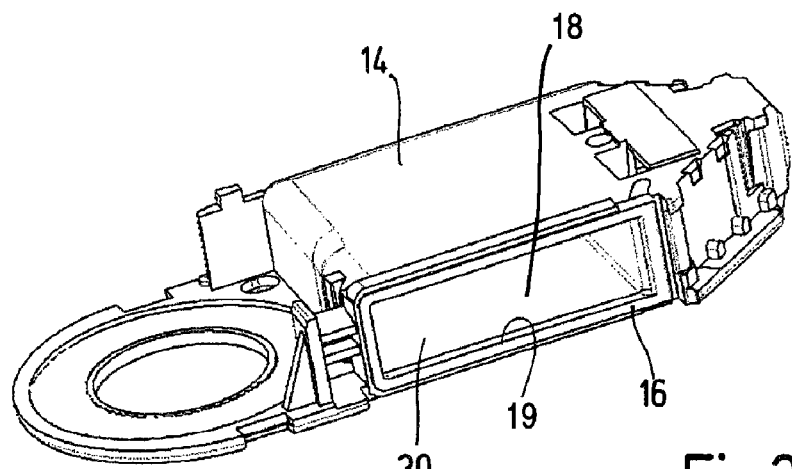
FIG. 3 shows a cassette container for the test tape cassette with a circumferential seal in a perspective view.
Figure 4:
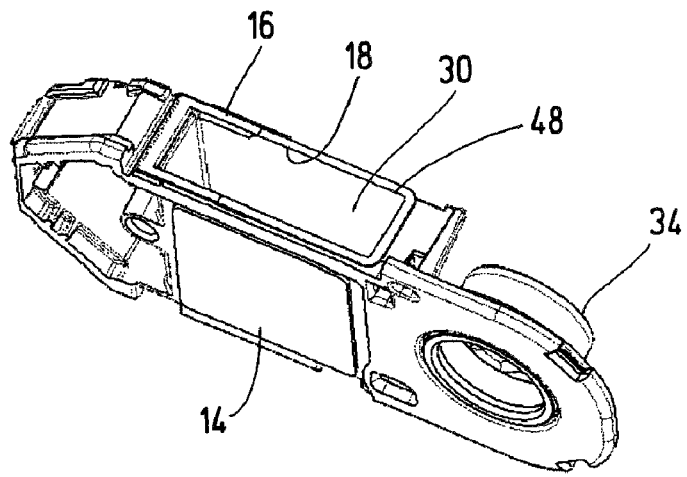
FIG. 4 shows a cassette container for the test tape cassette with a sealing segment in a perspective view.

As shown best in FIGS. 3 and 4, the opening 18 that can be closed by the closing foil 22 is dimensioned such that the test tape 10 in the form of supply roll 28 including possible desiccant-assembly functional parts can be completely inserted into the storage chamber 30 during the manufacturing process. A rectangular opening 18 is advantageously provided for this purpose where the length of the opening is larger than the initial diameter of the supply spool and its width is larger than the width of the test tape.

In the embodiment according to FIG. 3 a circumferential rectangular profile seal 19 which is preferably made of a TPE, is inserted into a corresponding edge recess. This creates a flat seal surface which simplifies the sealing on of the closing foil 22 in a material-tight manner outside the passage gap 20.

FIG. 4 shows a modification in which a sealing segment 16 is allocated to the tape passage whereas the remaining border or flat ring area 48 of the opening 18 is formed by walls of the container 14. Such a structure can be manufactured in a uniform process using a two-component injection-moulding technique. In this connection care must be taken that a firm tight joint is formed during the injection process by suitable selection of materials.

Figure 5:
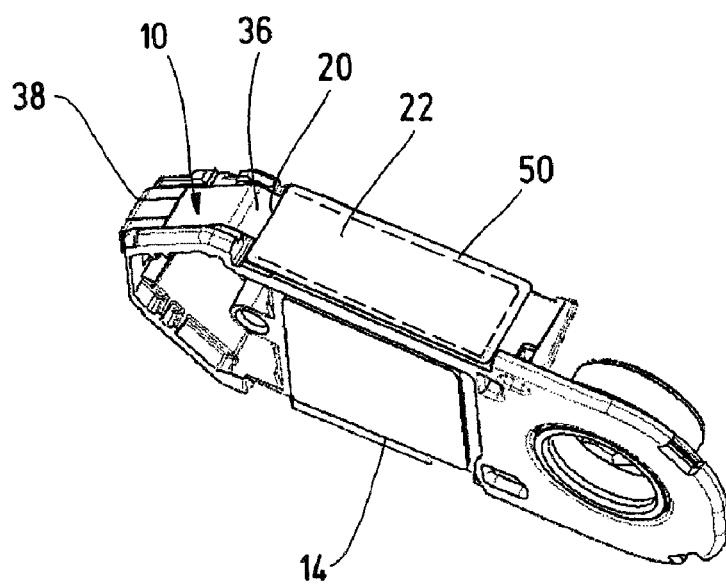
FIG. 5 shows the container according to FIGS. 4 and 5 sealed with a sealing foil.

The flat ring area 48 designed in this manner is heat-sealed according to FIG. 5 with a closing foil 22 along an approximately U-shaped seal strip 50. It is sealed either only on the sealing ring 16 (FIG. 3) or on the sealing segment 16 and simultaneously on the container material (FIG. 4). The thin flexible closing foil 22 can be formed by an aluminium foil the inner side of which is provided with a meltable heat seal coating. It should be ensured that the melting temperatures of all materials involved in the sealing process are at a uniform temperature level. In order to keep the passage gap 20 free, either the carrier tape 36 or an insert of a corresponding geometry can be sealed in during the heat-sealing process. During the heat-sealing a tight heat-seal joint between the container 14 or seal 16 and the heat-sealable inner side of the aluminium foil 22 is then formed on the entire surface of the flat ring area 48 with the exception of the inserted tape or insert. After the heat-sealing process, the carrier tape 36 which may also be adhesively joined, can be freed of slight adhesions by slightly transporting it forwards which is advantageously carried out when it is first used. If present, the insert is pulled out to thus expose the passage gap 20.

Figure 6:
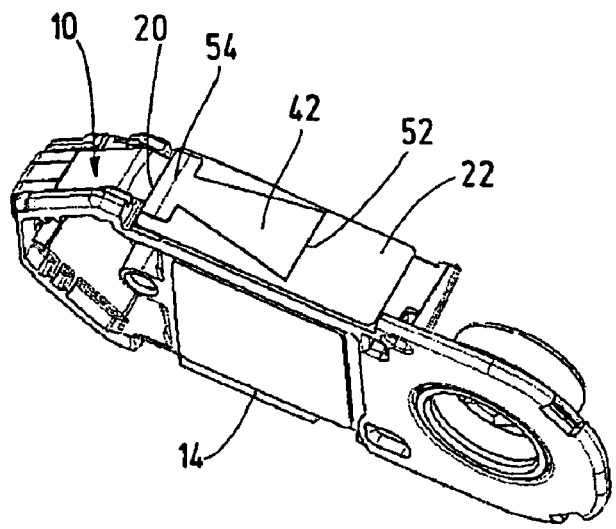
FIG. 6 shows the container according to FIG. 5 additionally with a pressing sealing element.

FIG. 6 also illustrates the function of the pressing element 42. This can be formed by a leaf spring one end of which 52 is supported on the cassette and the free end 54 of which with a wide area is pressed under pretension onto the closing foil over the passage gap 20. A high-grade steel spring can be used to minimize material fatigue even under alternating climatic stress.

Figure 7:
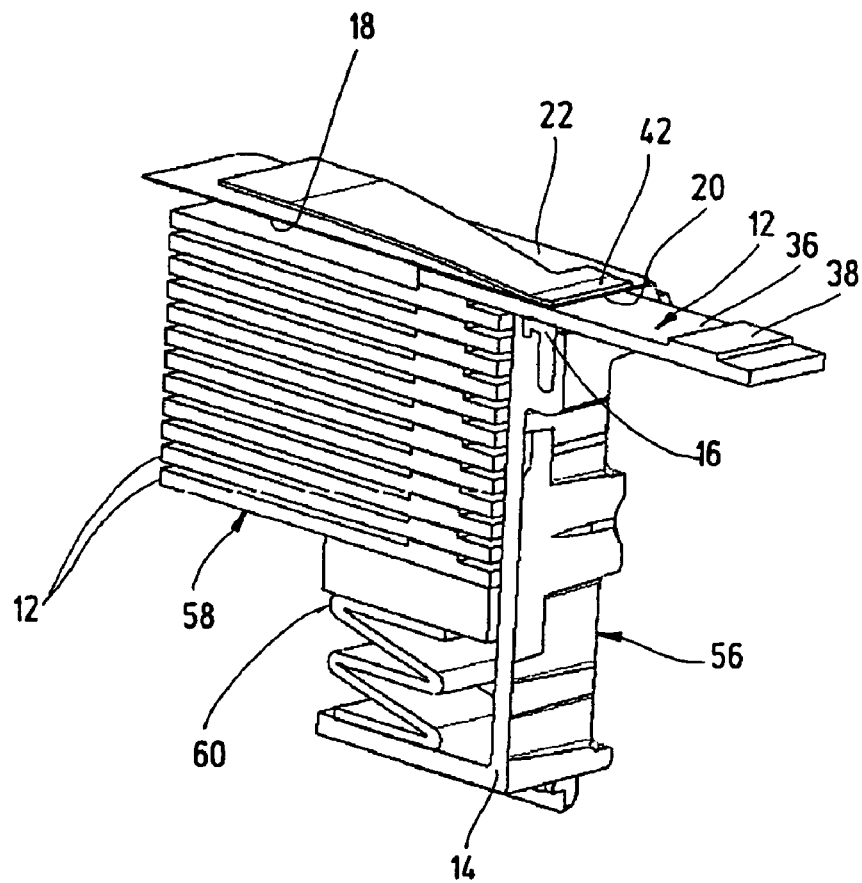
FIG. 7 shows a strip magazine for blood sugar tests with a foil seal in an opened sectional perspective.

A variant of the invention intended for the use of test strips 12 is shown in FIG. 7. The constructive design of the passage seal 16 and closing foil 22 essentially corresponds to the embodiment elucidated above so that the same reference numerals are used for the same parts. Instead of a tape cassette, a strip magazine 56 is provided of which only a section is shown and comprises a rectangular storage container 14 for holding a stack 58 of test strips 12. Each test strip 12 has a test field 38 on a section of a carrier tape 36 for applying the body fluid. The stack of strips 58 is inserted as a complete package through the opening 18 into the container 14 before the closing foil 22 is sealed on and then it is sealed in while keeping the passage gap 20 free by means of an insert. A spring mimic 60 is braced against the bottom of the container in order to reposition the stack towards the upper withdrawal area. In each case the upper strip 12 can be withdrawn by a push mechanism that is not shown by which means the particular strip is pushed out in the longitudinal direction of the strip through the passage gap 20 and is provided for use. In this connection the pressing element 42 is only lifted to dispense the strip whereas for the remaining time no strip 12 is present in the passage gap 20 and thus a high degree of tightness is ensured.

The tape cassette 24 as well as the strip magazine 56 can be exchanged as consumables in a holding drawer of a hand-held device in order to be able to automate the test process optionally including the sampling.

In summary the following can be stated: The invention concerns a diagnostic test unit for analysing a body fluid comprising a test carrier (test tape 10; test strip 12) provided with test fields 38 for the application of the body fluid and a container 14 containing the test carriers where an opening 18 of the container 14 is bordered at least in some areas by a seal 16. According to the invention it is proposed that the opening 18 is screened from the surroundings of the container 14 by a closing foil 22 and that the test tape 10 or a test strip 12 to be dispensed is passed through a passage gap 20 between the closing foil 22 and seal 16.

The invention claimed is:

1. A diagnostic test unit for analysing a body fluid in particular for blood sugar tests comprising:
    a test tape provided with test fields for applying the body fluid and a container containing the test tape, wherein an opening of the container for dispensing test tape is at least in some areas bordered by a seal, characterized in that the opening is screened by a closing foil from the surroundings of the container, wherein the closing foil is sealed onto a ring face on the container which borders the opening and at least one segment of the ring face is formed by the seal, and wherein the test tape is passed through a passage gap between the closing foil and the seal.

2. The test unit according to claim 1, characterized in that the test tape is inserted in the form of a tape roll through the opening into the container.

3. The test unit according to claim 1, characterized in that that the test tape has free carrier sections between successive test fields and that a test field-free carrier section is in the passage gap in a storage state.

4. The test unit according to claim 1, characterized in that the container is formed by a tape cassette wherein the test tape can be transported out of a storage chamber over an application site into a waste and the opening is located in the area of the storage chamber.

5. The test unit according claim 1, characterized in that that the rear side of the test tape facing away from the test fields glides over the seal.

6. The test unit according to claim 1, characterized in that the front side of the test tape carrying the raised test fields runs towards the border of the flexible closing foil.

7. The test unit according to claim 1, wherein the seal and the closing foil seal against the test tape.

8. The test unit according to claim 1, further comprising:
    a pressing element exerting surface pressure on the closing foil towards the seal.

9. The test unit according to claim 8, wherein the pressing element is a leaf spring.

10. The test unit according to claim 1, wherein the test tape and the closing foil extend in a generally parallel manner relative to one another.

11. A diagnostic test unit for analysing a body fluid in particular for blood sugar tests comprising:
    a plurality of test strips which each have at least one test field for applying the body fluid and a container for receiving the test strips wherein an opening of the container for individually dispensing test strips is bordered by a seal at least in some areas characterized in that the opening is screened by a closing foil from the surroundings of the container, wherein the closing foil is sealed onto a ring face on the container which borders the opening and at least one segment of the ring face is formed by the seal, and wherein the test strips can be passed through a passage gap between the closing foil and the seal for dispensing.

12. The test unit according to claim 11 characterized in that the test strips are introduced into the container through the opening as a stack of strips.

13. The test unit according to claim 11 characterized in that that the container is formed by a strip magazine where the test strips can be individually pushed out of a storage chamber.

14. The test unit according to claim 11, characterized in that the rear side of at least one of the test strips which faces away from the test field glides over the seal and the front side runs against the flexible closing foil when the test strip is dispensed.

15. The test unit according to claim 11 characterized in that the opening acts as an inlet for insert parts of the container before the closing foil is applied.

16. The test unit according to claim 11 characterized in that desiccants in the form of functional composite injection-moulded parts are introduced through the opening into the container.

17. The test unit according to claim 11 characterized in that the closing foil is held by a pressing element under surface pressure to minimize the passage gap towards the seal.

18. The test unit according to claim 17 characterized in that the pressing element comprises a spring.

19. The test unit according to claim 18, wherein the spring is a leaf spring.

20. The test unit according to claim 11 characterized in that when the closing foil is applied, the passage gap is kept free by a section of the test tape or of a test strip or by an insert.

21. The test unit according to claim 11 characterized in that the closing foil is joined along a sealing line with the container and/or the seal in a material-tight manner.

22. The test unit according to claim 11 characterized in that the closing foil is formed by a carrier material made of aluminium which is provided with a heat-seal coating.

23. The test unit according to claim 11 characterized in that the seal is designed as a single component injection-moulded part or in combination with the container as a two-component injection-moulded part formed from TPE.

24. The test unit according to claim 11 characterized in that the container which is loaded with the test tape or the test strips is stored in a tight outer packaging which is to be opened for use.

25. A diagnostic test unit for analysing a body fluid in particular for blood sugar tests comprising:
a test tape provided with test fields for applying the body fluid and a container containing the test tape, wherein an opening of the container for dispensing test tape is at least in some areas bordered by a seal characterized in that the opening is screened by a closing foil from the surroundings of the container, wherein the opening acts as an inlet for insert parts of the container before the closing foil is applied, and that the test tape is passed through a passage gap between the closing foil and the seal.

26. A diagnostic test unit for analysing a body fluid in particular for blood sugar tests comprising:
a plurality of test strips which each have at least one test field for applying the body fluid and a container for receiving the test strips wherein an opening of the container for individually dispensing test strips is bordered by a seal at least in some areas characterized in that the opening is screened by a closing foil from the surroundings of the container, wherein the opening acts as an inlet for insert parts of the container before the closing foil is applied, and that the test strips can be passed through a passage gap between the closing foil and the seal for dispensing.

27. A hand-held device for analysing a body fluid in particular for blood sugar tests comprising:
a receiving compartment to insert a diagnostic test unit; the test unit including
a plurality of test strips which each have at least one test field for applying the body fluid and a container for receiving the test strips wherein an opening of the container for individually dispensing test strips is bordered by a seal at least in some areas characterized in that the opening is screened by a closing foil from the surroundings of the container, wherein the opening acts as an inlet for insert parts of the container before the closing foil is applied, and that the test strips can be passed through a passage gap between the closing foil and the seal for dispensing.

* * * * *